(12) United States Patent
Bischoff et al.

(10) Patent No.: US 12,226,346 B2
(45) Date of Patent: Feb. 18, 2025

(54) METHOD FOR EYE SURGICAL PROCEDURE

(71) Applicant: Carl Zeiss Meditec AG, Jena (DE)

(72) Inventors: Mark Bischoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/313,030

(22) Filed: May 5, 2023

(65) Prior Publication Data

US 2023/0404803 A1 Dec. 21, 2023

Related U.S. Application Data

(63) Continuation of application No. 15/514,660, filed as application No. PCT/EP2015/072295 on Sep. 28, 2015, now abandoned.

(30) Foreign Application Priority Data

Sep. 29, 2014 (DE) ..................... 10 2014 014 566.2

(51) Int. Cl.
*A61F 9/008* (2006.01)
*A61F 9/00* (2006.01)
*A61F 9/007* (2006.01)

(52) U.S. Cl.
CPC ............... *A61F 9/008* (2013.01); *A61F 9/00* (2013.01); *A61F 9/007* (2013.01);
(Continued)

(58) Field of Classification Search
None
See application file for complete search history.

(56) References Cited

U.S. PATENT DOCUMENTS 5,766,171 A * 6/1998 Silvestrini .............. A61B 18/14
606/49
7,717,907 B2 5/2010 Ruiz et al.
(Continued)

FOREIGN PATENT DOCUMENTS

DE 695 00 997 T2 4/1998
DE 10 2007 019815 A1 10/2008
(Continued)

OTHER PUBLICATIONS

Aristeidou A, Taniguchi EV, Tsatsos M, Muller R, McAlinden C, Pineda R, Paschalis El. The evolution of corneal and refractive surgery with the femtosecond laser. Eye Vis (Lond). Jul. 1, 20154;2:12. doi: 10.1186/s40662-015-0022-6. PMID: 26605365; PMCID: PMC4655461. (Year: 2015).*
(Continued)

*Primary Examiner* — Lynsey C Eiseman
*Assistant Examiner* — James Moss
(74) *Attorney, Agent, or Firm* — DeWitt LLP

(57) ABSTRACT

The invention relates to a planning device for generating control data for a treatment apparatus, which by means of a laser device generates at least one cut surface in the cornea, and to a treatment apparatus having such a planning device. The invention further relates to a method for generating control data for a treatment apparatus, which by means of a laser device generates at least one cut surface in the cornea, and to a corresponding method for eye surgery. The planning device is thereby provided with calculating means for defining the corneal incision surfaces, wherein the calculation means determines the corneal incisions such that after inserting an implant into the cornea, existing refractive errors are counteracted.

6 Claims, 6 Drawing Sheets

(52) U.S. Cl.
CPC ...... *A61F 9/00825* (2013.01); *A61F 9/00827* (2013.01); *A61F 9/00831* (2013.01); *A61F 9/00834* (2013.01); *A61F 2009/00872* (2013.01); *A61F 2009/00878* (2013.01)

(56) References Cited

U.S. PATENT DOCUMENTS

| | | | |
|---|---|---|---|
| 9,408,747 B2 | 8/2016 | Wottke | |
| 2008/0275433 A1* | 11/2008 | Russmann | A61F 9/00829 606/5 |
| 2009/0187171 A1 | 7/2009 | Loesel | |
| 2010/0087802 A1* | 4/2010 | Bischoff | A61B 3/107 606/4 |
| 2011/0319876 A1* | 12/2011 | Feingold | A61F 9/00836 606/4 |
| 2012/0172854 A1 | 7/2012 | Raymond et al. | |
| 2020/0315847 A1* | 10/2020 | Rathjen | A61F 9/00827 |

FOREIGN PATENT DOCUMENTS

| | | |
|---|---|---|
| DE | 102012014769 A1 | 1/2013 |
| DE | 10 2007 019813 A1 | 3/2014 |
| DE | 10 2013 218 415 A1 | 4/2014 |
| DE | 102012022081 A1 | 5/2014 |

OTHER PUBLICATIONS

Quan Yan. Femtosecond Laser-Assisted Ophthalmic Surgery: From Laser Fundamentals to Clinical Applications. Micromachines. 2022; 13(10):1653. https://doi.org/10.3390/mi13101653 (Year: 2022).*

English translation of PCT International Preliminary Report on Patentability for International Application No. PCT/EP2015/072295, mailed Apr. 13, 2017, 10 pages.

PCT International Search Report and Written Opinion for International Application No. PCT/EP2015/072295, mailed Nov. 9, 2015, 12 pages.

English translation of PCT International Search Report for International Application No. PCT/EP2015/072295, mailed Nov. 9, 2015, 2 pages.

DE Search Report for DE 10 2014 014 566.2, dated Jun. 24, 2015, 8 pages.

Application and File History for U.S. Appl. No. 15/514,660, filed Mar. 27, 2017. Inventors: Mark Bischoff et al. as available on Patent Center at www.uspto.gov.

* cited by examiner

METHOD FOR EYE SURGICAL PROCEDURE

RELATED APPLICATIONS

This application is a continuation of application Ser. No. 15/514,660, filed Mar. 27, 2017, which in turn claims priority to PCT/EP2015/072295, filed Sep. 28, 2015 which is a national stage entry and claims priority to DE 10 2014 014 566.2, filed Sep. 29, 2014, each of the above applications being incorporated herein by reference in its entirety.

FIELD OF THE INVENTION

The invention relates to a laser treatment apparatus which produces at least one cut in the cornea by application of a laser device that includes a planning device that generates control data for the treatment apparatus.

The invention further relates to a method that generates control data for a treatment apparatus, which produces at least one cut in the cornea by application of the laser device and a method of ophthalmic surgery, wherein by use of a treatment apparatus at least one cut surface is produced in the cornea with a laser device.

BACKGROUND

Various treatment methods with the aim of correction of refraction of the human eye are known in the prior art. The aim of the surgical techniques is thereby to selectively alter the cornea in order to thus influence light refraction in the eye. To this end, several surgical techniques are used. The most common is currently so-called laser-assisted in situ keratomileusis, which is also abbreviated as LASIK. Here, a corneal lamella of the corneal surface is first detached on one side and folded aside. Detachment of this lamella can take place by use of a mechanical microkeratome, or also by application of a so-called laser keratome, such as is marketed by Intralase Corp., Irvine, USA, for example. After the lamella is detached and folded aside, the use of an excimer laser is provided during the LASIK operation, which removes the thus exposed corneal tissue under the lamella by of ablation. After the volume under the corneal surface is vaporized in this manner, the corneal lamella is folded back to its original place.

The use of a laser keratome to lift the lamella is advantageous in comparison with a mechanical knife, as this improves geometric precision and reduces the frequency of clinically relevant complications. In particular, a lamella with a very much more constant thickness can be produced when laser radiation is used. The cut edge is also precisely formed, which reduces the risk for disordered healing by these boundary layers which also remain after the operation. A disadvantage of this method, however, is the fact that two different treatment apparatuses must be used, firstly the laser keratome specifically to lift the lamella, and secondly the corneal tissue vaporizing laser.

These drawbacks have been eliminated in a process recently implemented by Carl Zeiss Meditec AG. In this method that is generally described as lenticular extraction, a cut geometry is formed in the cornea by application of a short-pulse laser, for example a femtosecond laser, which separates a corneal volume (a so-called lenticule) in the cornea. This is then manually removed by the surgeon. The advantage of this method lies firstly in that the cut quality is again improved through use of the femtosecond laser. Secondly, only one treatment apparatus is necessary; the excimer laser is no longer used.

A medically advantageous variation of the method is referred to in the literature as the SMILE method, in which no flap is created, but rather only a small opening cut serves as an access to the lenticule harbored under the so-called cap. The separated lenticule is removed through this small opening cut, so that the biomechanical integrity of the anterior cornea is less affected than with other methods. Additionally, in this way fewer superficial nerve fibers are cut in the cornea, which has a demonstrably favorable effect on the restoration of the original sensitivity of the corneal surface. The symptom of dry eye, often to be treated after LASIK, is thereby reduced in severity and duration. Other complications following LASIK, primarily associated with the flap (for example, wrinkles, epithelial growths in the flap bed), occur more rarely without the flap.

When generating cuts in the cornea by application of laser radiation, the optical radiation effect is typically exploited such that an optical breakthrough is generated by application of individual optical pulses whose duration may be between approximately 100 fs and 100 ns. It is also known to introduce individual pulses, the energy of which is below a threshold for an optical breakthrough, into the tissue or material overlaid in such a way that a separation of material or tissue is also thereby achieved. This concept of cut production in the corneal tissue allows a wide variety of cuts.

It is also state of the art to perform a correction of refraction by inserting an implant (also called an inlay) in the cornea of at least one eye of an affected patient. The implant can thereby be artificial by nature, e.g. a ring or a lens made of synthetic material (e.g. KAMRA®, Flexivue®), or also an appropriately shaped implant from a biomaterial or a graft from human corneal tissue.

It is hereby standard practice for the currently available implants to create a pocket-like section geometry (pocket) in the cornea by means of femtosecond laser keratome, which is intended for the inclusion of the implant and simultaneously supports the insertion of the implant by the physician.

Lenticular extraction methods principally offer good possibilities to be combined with an implant process by placing an implant into the inside of the cornea following the lenticule removal. The SMILE procedure also offers the possibility to utilize the pocket-like section geometry created as a result of the procedure for the inclusion of the implant and to thus provide a certain degree of mechanical stability.

SUMMARY OF THE INVENTION

It became evident, however, that the success of such a correction of refraction doesn't always meet the expectations and that a refractive error (even to a low degree) remains after the treatment. It is currently already feasible here to apply well-known surgical correction procedures (PRK or LASIK with Excimer laser) to correct the refraction of the affected eyes before or after the implantation of an inlay again. (Subsequent correction)

If the correction is done using one of the listed correction procedures, the ablation of tissue covering the implant and also the direct interaction of the therapy irradiation with the inlay represents a certain risk for the efficacy and safety of the overall procedure.

In a different field of ophthalmology, namely the treatment of presbyopia, it is known to introduce concentric cuts in the cornea to alter its mechanical stability. Such a solution is described in U.S. Pat. No. 7,717,907, for example, whereby the cuts go to a depth of 90% of the cornea thickness. These deep cuts cause change of curvature of the cornea through the interaction of the intraocular pressure and reduced counterforces in the entire cornea (induced keratoconus).

Embodiments of the invention provide a planning device for generating control data, a treatment apparatus for refraction-correcting ophthalmic surgery and a method for generating control data for such a treatment apparatus, facilitating a safe subsequent correction following the provision with a cornea implant.

Embodiments of the invention include a planning device of the aforementioned type, which has a calculating device for defining at least one corneal incision, wherein the calculating device determines the corneal incision so that existing refraction errors are counteracted after inserting an implant into the cornea.

The invention is further achieved with a treatment apparatus which has a laser device, which performs at least one incision in the cornea by application of laser radiation according to control data, and which has a planning device according to the aforementioned type for generating control data, wherein the planning device determines the corneal incisions so that existing refraction errors are counteracted after inserting an implant into the cornea.

Further, the invention is also achieved with a method for generating control data according to the type mentioned above, having: Generation of a control dataset for the corneal incisions for controlling the laser device, wherein the planning device determines the new corneal incisions so that existing refraction errors are counteracted after inserting an implant into the cornea.

The invention is finally also achieved with a method, comprising: Generating of a control dataset for the corneal incisions, transmission of the control data to the treatment apparatus and generating of the incisions through control of the laser device with the control dataset, wherein during generation of the control dataset the new corneal incisions are determined such that the existing refraction errors are counteracted after inserting an implant into the cornea.

The method per the invention and the respective device effects changes in the shape of the cornea through the interaction of the forces evoked by the implanted lenticel (implant) and the reduced counterforces in the anterior cornea of the caps, i.e. the part of the area located over the implant.

These cuts (hereinafter also referred to as relief cuts) are particularly inserted near Bowman's membrane and can cut through it. They don't reach any deeper than to the pocket cut, therefore no deeper than into the depth of the implant.

According to example embodiments of the invention it is advantageous, if the cuts do not reach any deeper into the cornea than 80% of the thickness of the cap. It is furthermore favorable, if the cuts run completely into the inside of the cornea. This prevents that openings are produced in the above-lying tissue that may have an unfavorable effect on the healing process.

The relief cuts are therefore, for example, designed so that epithelial cells can't diffuse deeply in case of a possible gaping. This may also be improved by that the cuts are not aligned or not aligned everywhere vertically to the surface. This can also be improved by that the cuts are not aligned or not aligned everywhere radially or circular with regard to the middle of the cornea.

The invention is not just suited for the improvement of the hyperopic correction. In similar fashion, it is also applicable for a myopia correction by lenticule transplant.

The invention may be used in connection with implants made of synthetics or organic material, but also in connection with transplants, particularly with transplanted lenticules.

The invention is not restricted to the cutting forms illustrated further. As long as the cuts match in terms of purpose, effective mechanism and approximate position, the method for its planning, creation, implementation and the respective devices is also used. Further cuts may also be used in astigmatism corrections or corrections of higher order visual defects, for example.

It goes without saying that the features previously mentioned and still needing to be explained can't just be used in the combinations set out, but also in other combinations or can be taken alone without leaving the framework of the invention.

BRIEF DESCRIPTION OF THE DRAWINGS

The invention is hereafter explained in more detail by way of example with reference to the accompanying drawings, which also disclose features essential to the invention.

DETAILED DESCRIPTION

Figure 1:
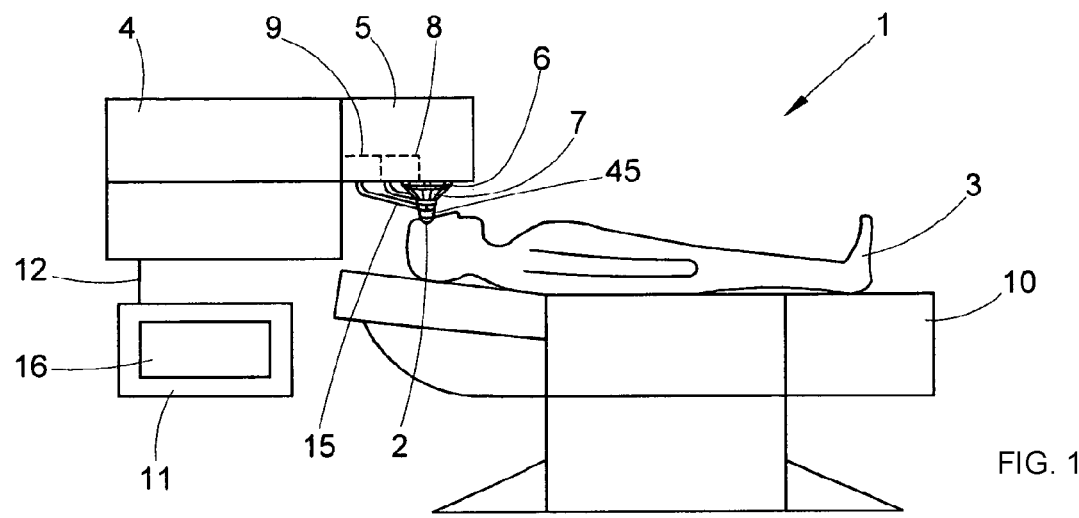
FIG. 1 is a schematic representation of a treatment apparatus with a planning device for treatment in ophthalmic surgical correction of refraction.

A treatment apparatus for ophthalmic surgery is represented in FIG. 1 and is provided with the general reference signs 1. The treatment device 1 is designed to apply laser cuts on an eye 2 of a patient 3. For this purpose, the treatment apparatus 1 comprises a laser device 4 that emits a laser beam 6 from a laser source 5, which is directed in the eye 2 or the eye cornea as a focused beam. The laser beam 6 is for example a pulsed laser beam with a wavelength between 300 nanometers and 10 micrometers. The pulse length of the laser beam 6 is furthermore in the range between 1 femtosecond and 100 nanoseconds, whereby pulse repetition rates of 50 to 50,000 kilohertz and pulse energies between 0.01 microjoules and 0.01 millijoules are feasible. The treatment apparatus 1 therefore creates a cut surface in the cornea of the eye 2 by deflecting the pulsed laser beam. A scanner 8 and a radiation intensity modulator 9 are therefore still intended in the laser device 4 or its laser source 9.

The patient 3 lies on a bed 10 that is adjustable in three directions in space to align the eye 2 appropriately to the incidence of the laser beam 6. In an example embodiment, the bed is motor-adjustable.

The control can take place by use of a control unit 11 in particular, which principally controls the operation of the treatment apparatus 1 and is thereby connected with the treatment apparatus by means of suitable data connections or connecting lines 12. This communication can naturally also take place in other ways, e.g. through light guides or via radio frequencies. The control unit 11 performs the respective settings, time control on the treatment device 1, particularly on the laser device, and thereby manages respective functions of the treatment apparatus 1.

The treatment apparatus 1 furthermore still comprises a fixing unit 15, which fixes the cornea of the eye 2 in its position across from the laser device 4. This fixing unit 15 can thereby comprise a well-known contact lens 45 that the eye cornea is placed against by of negative pressure and that gives the eye cornea a desired geometric shape. Such contact lenses are known from the state of the art, such as from DE 102005040338 A1. The disclosure content of this publication is incorporated herein by reference in so far as it affects the description of a design of the contact lens 45 possible for the treatment apparatus 1.

The treatment apparatus 1 furthermore comprises a camera not shown here, which can record an image of the eye cornea 17 through the contact lens 45. The lighting for the camera can hereby take place both in the visible and the infrared range.

The control unit 11 of the treatment apparatus 1 furthermore still comprises a planning device 16 that will still be clarified later on.

Figure 2:
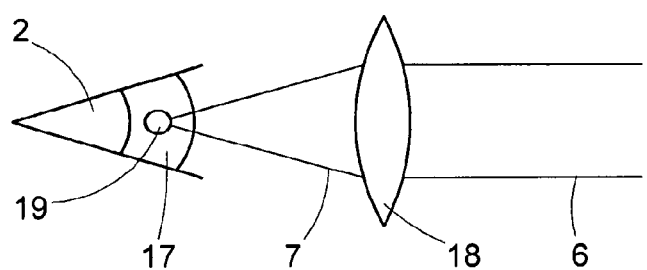
FIG. 2 is a schematic representation of the effect of the laser radiation which is used in the treatment apparatus of FIG. 1.

FIG. 2 shows schematically the mode of action of the incident laser beam 6. The laser beam 6 is focused and falls into the cornea 17 of the eye 2 as a focused laser beam 2. A schematically drawn in optic 18 is intended for the focusing. It effects a focus in the cornea 17, in which the laser beam energy density is so high that a non-linear effect occurs in the cornea 17 in combination with the pulse length of the pulsed laser beam 6. Each pulse of the pulsed laser beam 6 can create an optical breakthrough in the eye cornea 17 when in focus 19, for example, which in turn initiates a plasma bubble only schematically indicated in FIG. 2. During the formation of the plasma bubble, the separation of the layer of tissue comprises an area bigger than the focus 19, even though the conditions to create the optical breakthrough can only be achieved in the focus 19. So that an optical breakthrough is created from each laser pulse, the energy density, meaning the fluence of the laser beam must be above a certain, pulse-length dependent threshold value. One skilled in the art knows about this connection from DE 69500997 T2 for example. Alternately, a tissue-separating effect may also be achieved through pulsed laser radiation, by emitting several laser beam pulses in one area whereby the focus spots overlap. Several laser beam pulses then act together to achieve a tissue-separating effect. The type of tissue separation that is used by the treatment apparatus is however not further relevant for the following description; it is merely important that a cut creation takes place in the cornea 17 of the eye 2.

Figure 3:
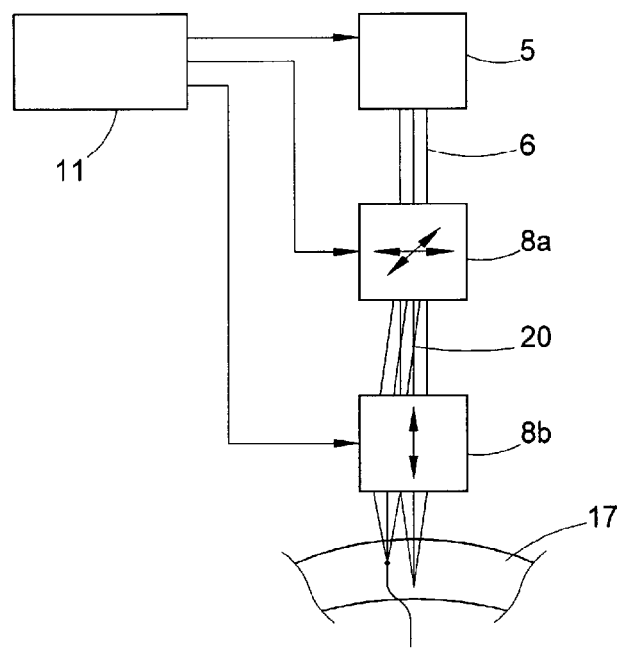
FIG. 3 is a further schematic view of the treatment apparatus of FIG. 1 with respect to the introduction of the laser radiation.

In order to perform an ophthalmic correction of refraction, a cornea volume is removed by application of laser radiation 6 from an area inside the cornea 17 by separating tissue layers, which isolate the cornea volume and then enable its removal. To isolate the cornea volume to be removed, in case the laser beam is brought in as a pulse, the location of the focus 17 of the focused laser beam 7 is shifted in the cornea 17. This is schematically shown in FIG. 3. The refractive properties of the cornea 17 are specifically changed by removing the volume in order to achieve the correction of refraction. The volume is therefore mostly lens-shaped and is referred to as lenticule. It is however sufficient for the present invention that the tissue layers are separated so that a pocket is formed to include the implant.

In FIG. 3, the elements of the treatment apparatus 1 are only recorded as far as they're required for the understanding of the cut creation. The laser beam 6, as already mentioned, is bundled in a focus 19 of the cornea 19, and the position of the focus 19 in the cornea is shifted so that focused energy from laser beam pulses is brought into the tissue of the cornea 17 in different areas for the cut creation. The laser beam 6 is preferably provided by the laser source 5 as pulsed radiation. The scanner 8 is constructed in two parts in the design of FIG. 3 and consists of a xy scanner 8a that is realized in one version by two essentially orthogonally deflecting galvanometer mirrors. The scanner 8a deflects the laser beam 6 originating from the laser source two-dimensionally, so that a deflected laser beam 20 is present after the scanner 9. The scanner 8a thus effects an adjustment of the position of the focus 19 essentially perpendicular to the main incidence direction from the laser beam 6 in the cornea 17. To adjust the depth, beside the xy scanner 8a, a z scanner 8b is still intended in the scanner 8 that is formed as an adjustable telescope, for example. The z scanner 8b ensures that the z position of the location of the focus 19, meaning its position on the optical axis of the incidence is changed. The z scanner 8b may be arranged subordinate or superordinate of the xy scanner.

The assignment of the individual coordinates to the direction in space is not essential for the functional principle of the treatment apparatus 1, just as little as that the scanner 8a deflects around axes that are orthogonal to each other. In fact, each scanner may be used that is able to adjust the focus 19 at a level at which the incidence axis of the optical radiation is not located. Any non-Cartesian coordinate systems may furthermore also be used for deflecting or controlling the position of the focus 19. Examples are spherical coordinates or cylindrical coordinates. The control of the position of the focus 19 is done by use of the scanners 8a, 8b while being controlled by the control unit 11, which performs respective adjustment on the laser source 5, the modulator 9 (not shown in FIG. 3), and the scanner 8. The control unit 11 enables suitable operation of the laser source 5 as well as the three-dimensional focus adjustment described here by way of example, so that a cut surface is formed ultimately, which isolates a specific cornea volume that is supposed to be removed for the correction of refraction.

The control unit 11 works based on specified control data, which are specified as target points for the focus adjustment in the laser system merely described here by way of example, for instance. The control data are usually comprised in a control data set. This one specifies geometric requirements for the cut surface to be formed as samples, such as the coordinates of the target points. In this embodiment, the control data set then also contains specific values for the adjusting mechanism of the focal position, e.g. for the scanner 8.

Figure 4:
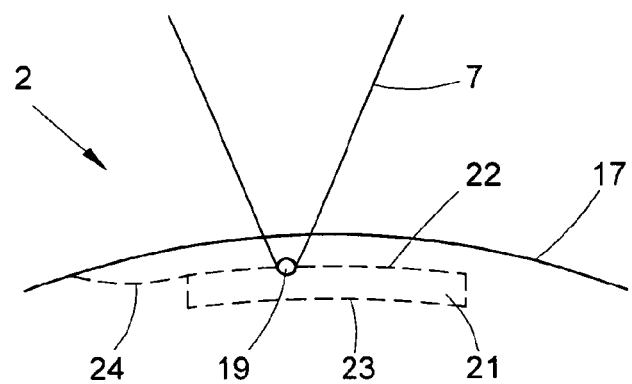
FIG. 4 is a schematic sectional view through the cornea to illustrate the removal of the corneal volume in connection with the ophthalmic surgical correction of refraction according to the state of technology.

The creation of the cut surface with the treatment apparatus 1 is shown as example in FIG. 4. A cornea volume 21 in the cornea 17 is isolated by adjusting the focus 19, in which the focused beam 7 is bundled. Cut surfaces are formed for this purpose, which by way of example, are formed here as an anterior flap cut surface 22 as well as a posterior lenticular cut surface 23. These terms are merely to be understood as an example and shall create the reference to the conventional Lasik or Lenticular Extraction procedures (SMILE) that the treatment apparatus 1 is also designed for, as already stated. What is merely important here, is that the cut surfaces 22 and 23 as well as no further specified edge cuts, which join the cut surfaces 22 and 23 on their edges, isolate the cornea volume 21. By use of an opening cut 24, a corneal lamella limiting the cornea volume on the anterior can be folded aside so that the corneal volume 21 can be removed. This corneal lamella defined by the anterior cut has a constant thickness in the preferred version, but may also have an inhomogeneous thickness, particularly a radius-dependent thickness.

Alternatively, the SMILE procedure can be used, in which the corneal volume 21 is removed through a small opening cut as is described in DE 10 2007 019813 A1. The disclosure content of this publication is incorporated by reference here. An implant (inlay) can then be inserted in the pocket created in this or a different manner.

Figure 5:
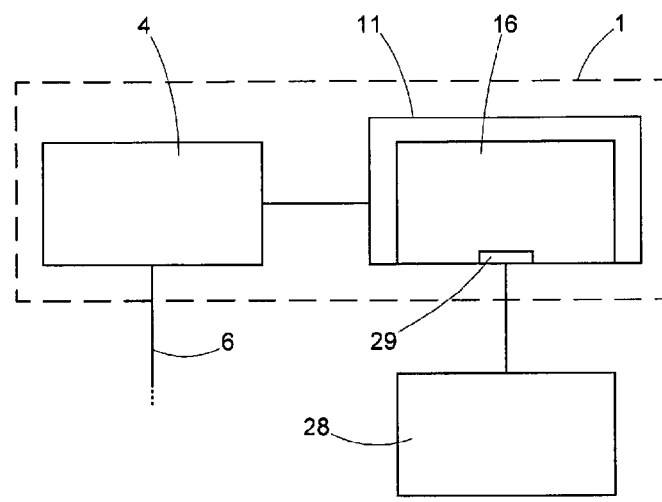
FIG. 5 is a schematic representation in view of the structure of the treatment unit of FIG. 1 with particular reference to the planning device present there.

FIG. 5 shows schematically the treatment apparatus 1, with reference to which the significance of the planning device 16 shall be described. In this version, the treatment apparatus 1 has at least two devices or modules. The already described laser device 4 emits the laser beam 6 onto the eye 2. The operation of the laser device 4 thereby takes place, as already stated, fully automatically by operation of the control unit 11, meaning the laser device 4 starts the creating and deflecting of the laser beam 6 on a respective start signal and thus creates cut surfaces that are established in the manner described. The laser device 5 receives the control signals required for the operation from the control unit 11, which had respective control data provided for it beforehand. This is done by use of the planning device 16, which is shown for example in FIG. 5 as part of the control unit 11. The planning device 16 can naturally also be formed separately and may communicate with the control device 11 on a wired or wireless basis. It is then merely needed that a respective data transmission channel exist between the planning device 16 and the control unit 11.

The planning device 16 creates a control data set that is provided for the control unit 11 to execute the ophthalmic surgical correction of refraction. The planning device thereby uses measured data regarding the cornea of the eye. In the embodiment described here, this data comes from a measuring device 28 that has measured the eye 2 of the patient 2 beforehand. The measuring device 28 may naturally be formed in any manner and may transmit the respective data to the interface 29 of the planning device 16.

The planning device now supports the operator of the treatment apparatus 1 during the determination of the cut surface for isolating the corneal volume 21 or the creation of a pocket for an implant or during the creation of the relief cuts per the invention. This can go on to a fully automatic determination of the cuts, which can be effected, for example, by that the planning device 16 determines the corneal volume 21 to be removed from the measurement data for example, and which uses it to create respective control data for the control device 11. The planning device 16 may include input options on the other side of the level of automation, on which a user enters the cuts in the form of geometrical or optical parameters (refractive powers or keratometric changes) or mechanical parameters (elasticity), or where these are automatically derived from diagnosis data. Intermediate stages may be included for suggestions for the cuts, which the planning device 16 generates automatically and which can then be modified by an operator. All these concepts that were already explained above in the more general descriptive part may basically be used here in the planning device 16.

In order to perform a treatment, the planning device 16 creates control data for the cut creation, which are then used in the treatment apparatus 1.

Figure 6A:
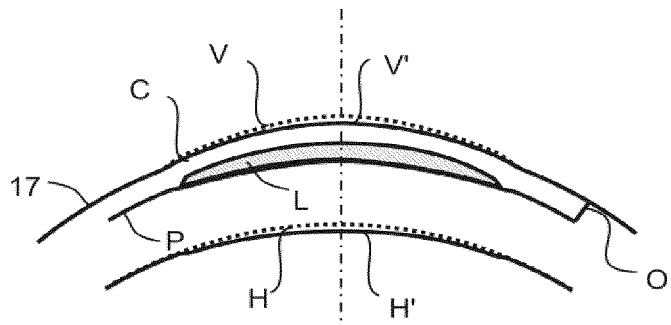
FIGS. 6A and 6B are schematic representations for the purposes of illustration of the insertion of an inlay in connection with an ophthalmic surgical correction of refraction according to state of technology.
Figure 6B:
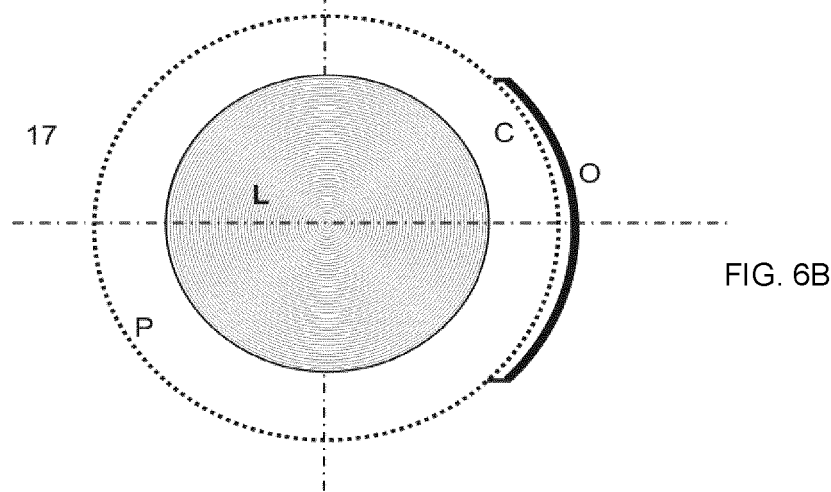

FIG. 6a shows a schematic representation of a cut geometry for a pocket per the state of the art of technology to clarify the geometric relationships in cross section. The cornea 17 has a pocket cut P with an opening cut O under the cap C. An inlay L is inserted through the opening cut O. The inlay L thereby changes the geometry of the cornea 17 by deforming the front of the corneal front V. A possible explanation for the detected deviations between the target and the actual refraction after the implantation of an inlay could be due to the fact that the corneal rear side also deforms from H to H', but the corneal front side reacts mechanically and only displays a deformation V' deviating from the target deformation V, and a refraction condition is created different from the one desired. FIG. 6B shows a top view of the cornea represented in FIG. 6A.

In order to counteract this undesired deviation of the target geometry, additional relief cuts are applied in the cornea above the cap C.

The cut geometries according to embodiments of the invention are described in detail below.

Figure 7A:
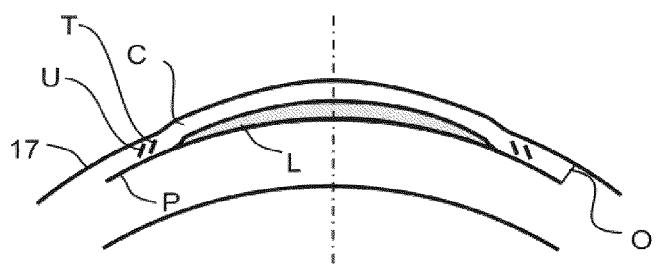
FIGS. 7A and 7B are schematic representations to demonstrate the invention.
Figure 7B:
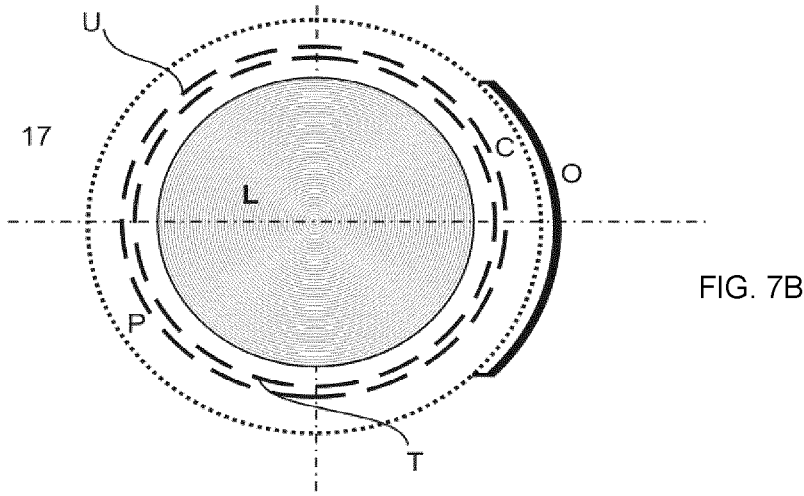

FIG. 7A depicts a schematic representation of a first cut geometry per the invention in cross section. The relief cuts T and U are thereby executed as circular arc segments, which run symmetrically around the optically effective zone of the eye. FIG. 7B shows a top view on the cornea represented in FIG. 7A.

Figure 8A:
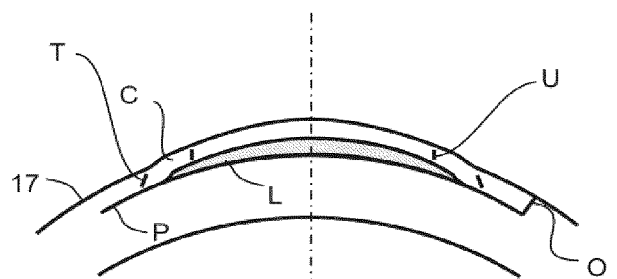
FIGS. 8A and 8B are schematic representations to demonstrate the invention in a second embodiment.
Figure 8B:
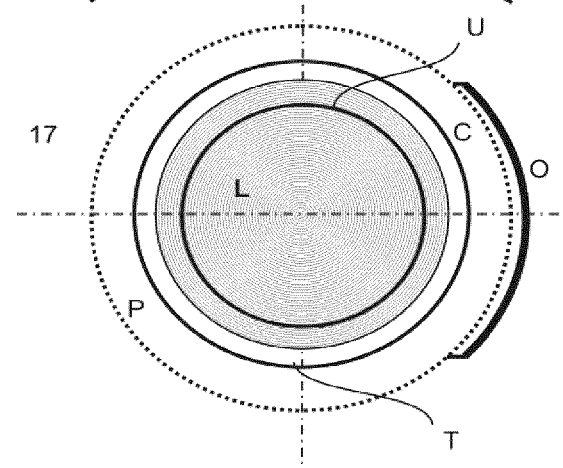

FIG. 8A depicts a schematic representation of a second cut geometry according to an example embodiment of the invention in cross section. The relief cuts T and U are thereby executed as complete circular arcs, which run outside of the optically effective zone of the eye. The relief cuts effect a more efficient deformation of the front side of the cornea and reduce the deformation of the rear side of the cornea. FIG. 8B shows a top view on the cornea represented in FIG. 8A.

Figure 9A:
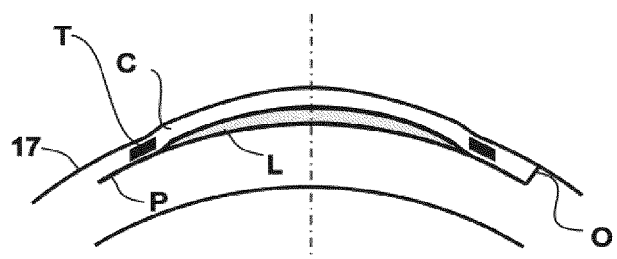
FIGS. 9A and 9B are schematic representations to demonstrate the invention in a further embodiment.
Figure 9B:
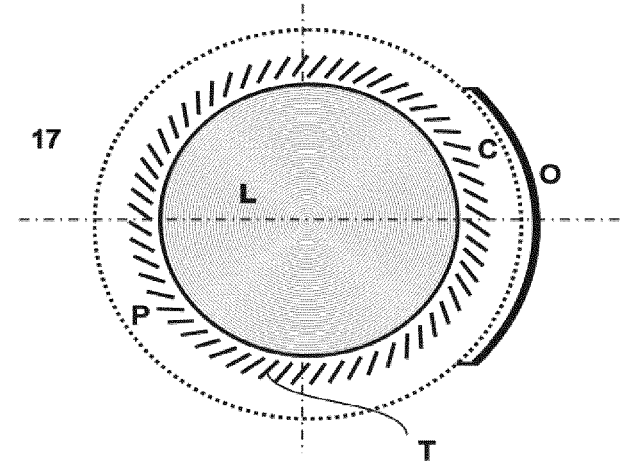

FIGS. 9A and 9B depict a schematic representation of another cut geometry according to an example embodiment of the invention in cross section. The relief cuts T are thereby executed as diagonally radially extending cuts. This cut variant may encourage the tissue expansion intended in the cap. FIG. 9B shows a top view of the cornea represented in FIG. 9A.

Figures 10A, 10B:
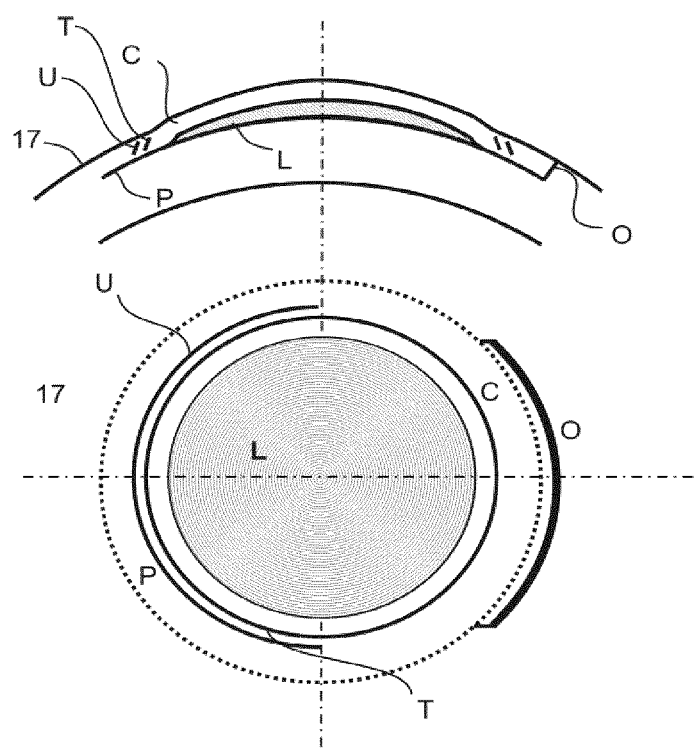
FIGS. 10A and 10B are schematic representations to demonstrate the invention in a further embodiment in connection with an astigmatism correction.

FIGS. 10A and 10B depict a schematic representation of another cut geometry in cross section as a variation to the geometry represented in FIG. 8. Astigmatism is corrected here through a circular arc cut U running asymmetrically relative to the eye's axis. FIG. 10B shows a top view of the cornea represented in FIG. 10A.

Figures 11A, 11B, 11C:
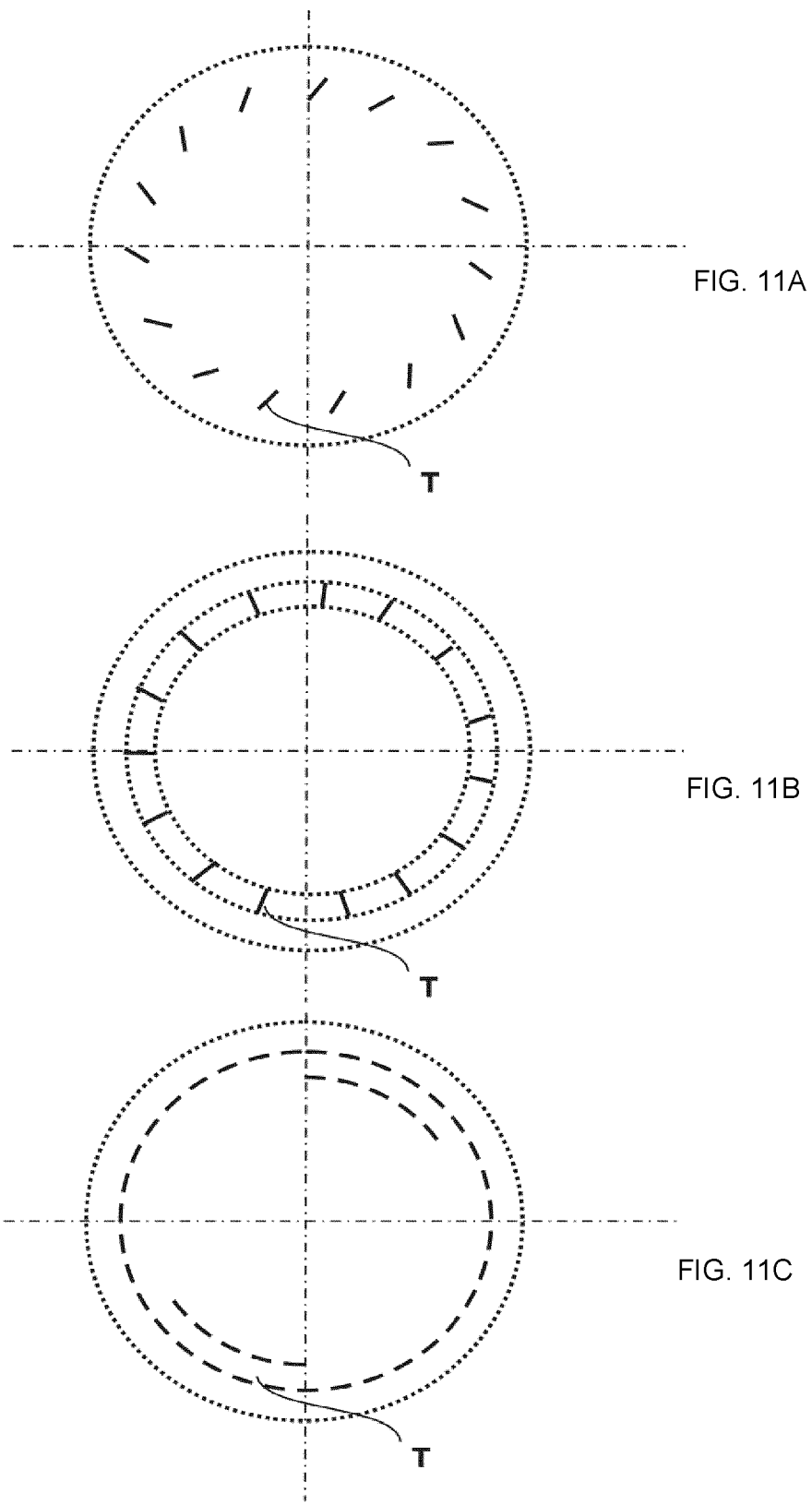
FIGS. 11A, 11B and 11C are schematic representations of various other cut geometries.

More possible cut geometries for the relief cuts T are represented in FIGS. 11A and 11B. Depending on the type and extent of the tissue expansion strived for; these cut variants enable a better predictability of the result of the procedure and an accelerated healing. The astigmatism correction from FIGS. 10A and 10B are represented in FIG. 11C in combination with the cut from the circular arcs according to FIGS. 8A and 8B.

As can be gathered from the figures, the relief cuts T or U don't extend to the anterior corneal surface to prevent the risk of tearing or gaping. To facilitate mechanical stability, they don't extend to the inlay L either. With a given thickness d (between 140 μm and 200 μm) of the cap C, it is mostly favorable, if the cuts have a maximum depth extension of 0.8×d. It can however also be particularly advantageous in special cases, if relief cuts T or U extend to the inlay L.

It should also be mentioned that the treatment apparatus 1 or the planning device 16 naturally also concretely realizes the implementation of the previously generally explained procedure.

Another example embodiment of the planning device exists in the form of a computer program or a respective data carrier with a computer program, which realizes the planning device on a respective computer, so that the input of the measurement data takes places through suitable data transmission to the computer, and so that the control data is transmitted from this computer to the control unit 11.

The invention claimed is:

1. A method of ophthalmic surgery, wherein at least one cut is made in a cornea by application of a treatment device with a laser device, comprising:
    providing corneal data, based on data of a correction of refraction;
    determining a pocket cut in the cornea, the pocket cut being configured to receive an implant therein and having a cap overlying the pocket cut;
    determining at least one corneal relief cut on the basis of the corneal data, and
    creating a control data set for the at least one corneal relief cut; and
    transmitting the control data to the treatment device and creating the at least one corneal relief cut by controlling the laser device with the control data set to generate the at least one corneal relief cut to a depth less than a thickness of the cap overlying the pocket cut in the cornea and located in the cap overlying the pocket cut;
    wherein the at least one corneal relief cut is determined so that existing refractive errors are counteracted after inserting an implant in the cornea.

2. The method according to claim 1, further comprising determining the at least one corneal relief cut such that the at least one corneal relief cut reaches no deeper than 80% of the thickness of the cap over the implant in the cornea.

3. The method according to claim 1, further comprising determining the at least one corneal relief cut such that the at least one corneal relief cut is located above the implant when the implant is placed in the pocket cut.

4. The method according to claim 1, further comprising creating the control data set such that the at least one corneal relief cut comprises at least one circular arc segment.

5. The method according to claim 1, further comprising creating the control data set such that the at least one corneal relief cut comprises at least one circular arc.

6. The method according to claim 1, further comprising creating the control data set such that the at least one corneal relief cut comprises at least one radial extending or diagonally radial extending cut.

* * * * *

UNITED STATES PATENT AND TRADEMARK OFFICE
CERTIFICATE OF CORRECTION

PATENT NO. : 12,226,346 B2
APPLICATION NO. : 18/313030
DATED : February 18, 2025
INVENTOR(S) : Bischoff et al.

Page 1 of 1

It is certified that error appears in the above-identified patent and that said Letters Patent is hereby corrected as shown below:

On the Title Page

Item (56) under "OTHER PUBLICATIONS", in Column 2, Line 3, delete "Jul. 1, 20154;2:12." and insert --Jul. 14, 2015; 2:12.--

Item (57) under "Abstract", in Column 2, Line 11, delete "determines" and insert --determine--

In the Specification

Column 1, Line 7, delete "2017" and insert --2017, now abandoned,--

Column 1, Line 44, delete "by of" and insert --by--

Column 1, Line 53, delete "risk for" and insert --risk of--

Column 3, Line 66, delete "circular" and insert --circularly--

Column 4, Line 54, delete "correction" and insert --correction.--

Column 5, Line 29, delete "by of" and insert --by--

Column 5, Line 47, delete "drawn in" and insert --drawn--

Column 7, Line 67, delete "by that the" and insert --by the--

Column 7, Line 67, delete "determines" and insert --which determines--

Column 8, Line 42, delete "view on" and insert --view of--

Column 8, Line 51, delete "view on" and insert --view of--

Signed and Sealed this
Thirteenth Day of May, 2025

Coke Morgan Stewart
*Acting Director of the United States Patent and Trademark Office*